(12) United States Patent
Dreibholz et al.

(10) Patent No.: US 11,561,183 B2
(45) Date of Patent: Jan. 24, 2023

(54) TEST ELEMENTS AND METHODS OF PRODUCING THE SAME FOR STUDYING A BODY FLUID SAMPLE

(71) Applicant: Roche Diabetes Care, Inc, Indianapolis, IN (US)

(72) Inventors: Joerg Dreibholz, Altrip (DE); Herbert Fink, Mannheim (DE); Volker Huellen, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 405 days.

(21) Appl. No.: 15/841,524

(22) Filed: Dec. 14, 2017

(65) Prior Publication Data

US 2018/0106726 A1    Apr. 19, 2018

Related U.S. Application Data

(63) Continuation of application No. 14/010,683, filed on Aug. 27, 2013, now Pat. No. 9,874,525, which is a continuation of application No. PCT/EP2012/000653, filed on Feb. 11, 2012.

(30) Foreign Application Priority Data

Mar. 3, 2011  (EP) .................................. 11001784

(51) Int. Cl.
*G01N 21/78*  (2006.01)
*G01N 33/52*  (2006.01)

(52) U.S. Cl.
CPC ........... *G01N 21/78* (2013.01); *G01N 33/525* (2013.01)

(58) Field of Classification Search
CPC ............................. G01N 21/78; G01N 33/525
See application file for complete search history.

(56) References Cited

U.S. PATENT DOCUMENTS

| | | | | |
|---|---|---|---|---|
| 5,063,153 A | * | 11/1991 | Arai .......................... | C12Q 1/32 422/423 |
| 5,215,716 A | * | 6/1993 | Arai ..................... | G01N 33/525 422/423 |
| 5,679,042 A | * | 10/1997 | Varona ..................... | D04H 3/16 156/84 |
| 2004/0223926 A1 | | 11/2004 | Kobayashi | |
| 2005/0186109 A1 | | 8/2005 | Nakamura et al. | |
| 2006/0222675 A1 | * | 10/2006 | Sabnis .................... | A61F 13/42 424/405 |

FOREIGN PATENT DOCUMENTS

| | | |
|---|---|---|
| EP | 0051183 A1 | 5/1982 |
| EP | 0254202 A1 | 1/1988 |
| EP | 0524596 A1 | 1/1993 |

(Continued)

*Primary Examiner* — Samuel P Siefke
(74) *Attorney, Agent, or Firm* — Quarles & Brady, LLP

(57) ABSTRACT

Disclosed herein are methods of producing a test element for studying a body fluid sample. In the methods, a detection layer is covered with a polymeric spreading layer and applied to a support. The spreading layer can be produced by being sprayed onto the detection layer such that the spreading layer has a thickness of at most about 20 μm. Also disclosed are test elements produced by the methods, as well as tape cassettes incorporating such test elements.

8 Claims, 3 Drawing Sheets

(56) References Cited

FOREIGN PATENT DOCUMENTS

Figure 1:
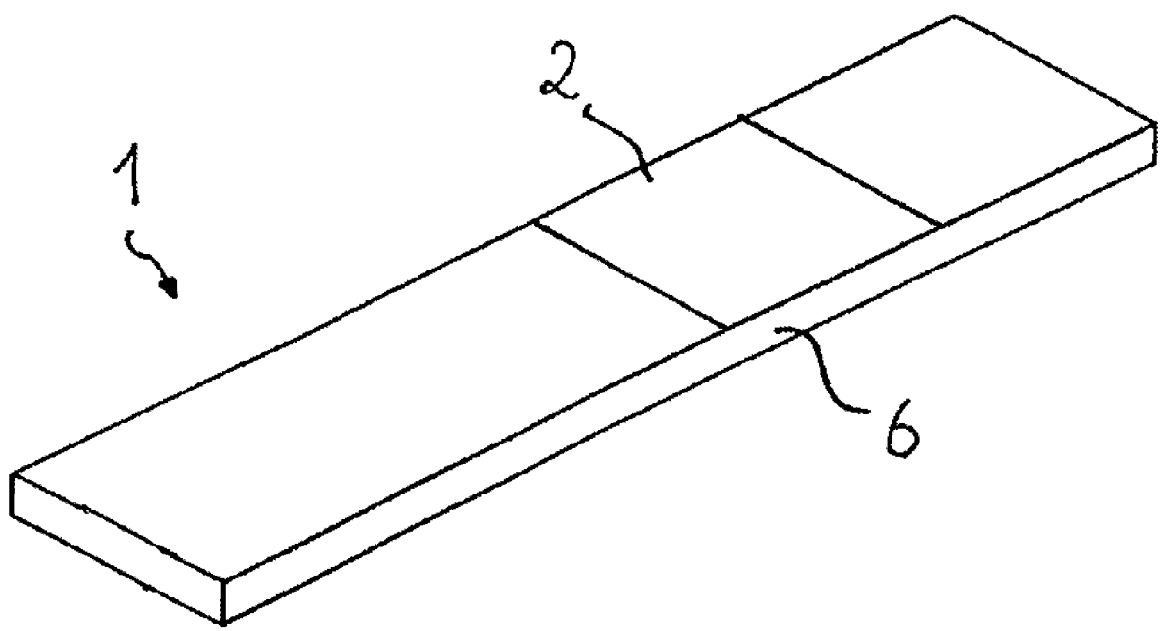

| | | | |
|---|---|---|---|
| EP | 1795891 | A1 | 6/2007 |
| EP | 2116180 | A1 | 11/2009 |
| EP | 2267446 | A1 | 12/2010 |
| EP | 2284534 | A1 | 2/2011 |
| WO | 2002/030478 | A3 | 4/2002 |

* cited by examiner

11,561,183 B2

TEST ELEMENTS AND METHODS OF PRODUCING THE SAME FOR STUDYING A BODY FLUID SAMPLE

CROSS-REFERENCE TO RELATED APPLICATIONS

This application is a continuation of U.S. patent application Ser. No. 14/010,683 filed Aug. 27, 2013, which is a continuation of International Patent Application PCT/EP2012/000653 filed Feb. 11, 2012, which claims benefit of European Patent Application 11001784.5 filed Mar. 3, 2011, which is incorporated herein by reference in its entirety.

TECHNICAL FIELD

The invention relates generally to engineering and medicine, and more particularly to methods of producing test elements for testing a body fluid sample, as well as the test elements themselves.

BACKGROUND

Conventional test elements include a support, usually made of a plastic material or paper that bears a detection layer with detection reagents, which effect a detection reaction when exposed to an analyte such as, for example, glucose or lactate. In detection reactions for photometric determination of an analyte concentration, it is advantageous to spread a body fluid sample, such as blood, on and/or in the detection layer as much as possible. For this reason, it is customary to apply a spreading layer onto the detection layer to facilitate spread of a body fluid sample droplet that has been applied.

For acceptable spreading behavior of the body fluid droplet, the spreading layer has a hydrophilic surface. Likewise, the spreading layer needs to be characterized by a high permeability (i.e., needs to be porous) to allow the body fluid droplet to easily reach the detection layer situated below the spreading layer.

Spreading layers made of fibrous material exhibit desired properties in this context. One disadvantage of fibrous spreading layers, however, is that the requisite manufacturing effort is high to prevent significant variation of the spreading behavior. This disadvantage can be largely circumvented by laminating a porous plastic membrane onto the detection layer to serve as the spreading layer. Such a test element is disclosed in, for example, US Patent Application Publication No. 2005/0186109.

Laminating, however, has its own disadvantages. Most notably, it induces a mechanical stress upon the detection layer and support of the test element. This mechanical stress can cause damage to the resulting test element.

As such, there is a need for additional methods for producing test elements having spreading layers.

BRIEF SUMMARY

Disclosed herein are methods of producing test elements by spraying the spreading layer onto a detection layer, as well as test elements resulting therefrom.

In one aspect, a method is disclosed for producing test elements that includes at least the step of spraying onto a detection layer a membrane as a spreading layer. This step being associated with a number of advantages, where:

Spraying the membrane to serve as the spreading layer produces significantly less mechanical stress upon the detection layer containing detection reagents when compared to conventional means such as application of a plastic membrane by laminating or application of a fibrous material membrane by gluing.

A sprayed spreading layer shows enhanced adhesion to the detection layer below it. For this reason, a test element produced by the methods described herein has increased bond strength. Applying a membrane by spraying attains improved adhesion, and thus simplifies test element production significantly. The sprayed spreading layer can be provided in, for example, a membrane-like manner or to form a nonwoven fabric. In contrast, spreading layers of plastic membranes or fibrous material membranes applied by laminating or gluing tend to detach from the detection layer, at least in regions thereof.

Advantageously, sprayed spreading layers can be easily produced and can be produced at very low production tolerances. For example, when compared to spreading layers made of fibrous material, sprayed spreading layers as described herein have a more homogeneous structure. Likewise, and when compared to laminated plastic membranes, sprayed spreading layers possess consistently better quality. Moreover, laminated plastic membranes typically are associated with a certain risk of damaging the membrane, where the risk of damage due to stretching, crack formation or the like is the more pronounced the thinner the plastic membrane is.

Sprayed spreading layers as described herein advantageously have a lower thickness when compared to conventional spreading layers. For example, due to its structure, spreading layers made of fibrous materials can be produced only in the form of relatively thick layers. Likewise, laminated plastic membranes are problematic when the thickness of the layer is less than 100 µm and reaches a limit when the thickness of the layer is 50 µm. Thinner plastic membranes necessarily are damaged when applied by laminating. In contrast, sprayed spreading layers as described herein can have a thickness of less than about 20 µm, less than about 12 µm, or even less than about 10 µm. Alternatively, the thickness of such spreading layers can be about 1 µm to about 12 µm, about 1 µm to about 10 µm, or even about 5 µm to about 10 µm.

Thinner spreading layers are advantageous in that a body fluid sample can reach the detection layer situated below it more rapidly. By using a thinner spreading layer, a larger fraction of a body fluid sample is available for the actual detection reaction, as the thinner spreading layer takes up a smaller fraction of a sample than a thicker spreading layer.

Because the thinner spreading layers as described herein have enhanced adhesion on the detection layer, it is therefore easier to implement test elements in the form of a tape that supports multiple test fields. For example, the test elements can be wound up into a reel and incorporated into tape cartridges. As such, test elements produced according to the methods described herein can be reeled up into a thinner reel diameter. In this manner, test elements provided in the form of tape cartridges can be provided either to be more compact or to allow a larger number of sample tests to be performed.

The properties of the sprayed spreading layer can be optimized through adjusting spraying parameters such as humidity, temperature, spraying distance and spraying rate. Whereas testing of plastic membranes that have different properties and are applied by laminating is always quite cumbersome, spraying parameters can be varied with negligible effort. Therefore, the properties of a sprayed spreading layer for a given application (i.e., a desired detection reaction), as well as the type and amount of body fluid sample, can be optimized in an advantageous manner.

An advantageous refinement described herein is that the methods provide for the molecules forming the spreading layer to be sprayed together with a carrier liquid, which evaporates subsequently (i.e., after or during the application by spraying). Basically, the carrier liquid can be used for the molecules that then form the spreading layer. In this manner, application by spraying can be simplified significantly.

It is feasible just as well to dispense with the supporting carrier liquid by applying the molecules forming the spreading layer as monomers or polymers in liquid form onto the detection layer. A change of temperature or addition of a polymerization and/or cross-linking agent then can lead to the solidification of the film of liquid applied by spraying. Polymerization and/or cross-linking of monomers or polymers through a change of temperature or by addition of a polymerization and/or cross-linking agent also can be used when monomers and/or polymers are first sprayed onto the detection layer together with a liquid, for example, in the form of a solution or an emulsion, which subsequently evaporates. In this context, the liquid applied by spraying may already contain a polymerization and/or cross-linking agent. It is feasible just as well to apply the polymerization and/or cross-linking agent in a second spraying process.

The molecules, which form the spreading layer, and the liquid, in combination with which they are applied by spraying, together can form the emulsion. In one embodiment, the spreading layer is produced by spraying the emulsion. Accordingly, during the spraying process, monomers and/or polymers forming the spreading layer are dissolved in a liquid that evaporates after spraying.

In some embodiments, the liquid, in combination with which the molecules forming the spreading layer are applied by spraying, is an organic liquid. In other embodiments, the organic liquids are polar organic solvents such as aliphatic polar organic solvents (e.g., aliphatic alcohols, ketones, and ethers or mixtures thereof), including methanol, acetone and tetrahydrofuran.

Advantageously, polar organic solvents readily evaporate and can dissolve a number of polymers that are well-suited for the spreading layer such as, for example, polyethylene glycol, polyvinylalcohol or cellulose, including modified cellulose such as hydroxypropylcellulose, cellulose nitrate or cellulose acetate.

It is another advantage of polar organic solvents, such as alcohol, that an adverse impact on the detection layer can be prevented particularly well by this means. Since body fluid samples are aqueous liquids, the detection layers of test elements usually contain detection reagents that are water-soluble or at least reactive to the presence of water. As such, polar organic solvents, such as alcohols, pose no problem in this context.

Another advantageous refinement described herein is the use of a pneumatic nozzle for spraying, which nebulizes a liquid by means of a pressurized gas. Accordingly, pneumatic nozzles expel a mixture of the nebulized liquid and a pressurized gas. Pneumatic nozzles quite often are referred to as two-component nozzles. Pneumatic nozzles allow for a very fine nebulization of liquids and a very homogeneous application by spraying. Compressed air or nitrogen can, for example, be used as the gas.

A sprayed spreading layer can be subjected to further steps, if needed. For example, a hydrophilic substance such as a surfactant can be embedded in the layer to further improve its spreading behavior. Such a hydrophilic substance, however, already may be contained in the solution or suspension applied by spraying and can be applied by spraying together with the layer. In this manner, a very homogeneous distribution can be attained in the layer.

In another aspect, a test element is disclosed for photometric testing of a body fluid sample. The test element includes a support, a detection layer containing detection reagents, and a polymeric spreading layer that covers the detection layer and that has a thickness of no more than about 20 μm, about 12 μm, or about 10 μm. Alternatively, the thickness of the polymeric spreading layer can be from about 1 μm to about 12 μm, about 1 μm to about 10 μm, or about 5 μm to about 10 μm. The test element can be produced according to the methods described herein. Comparable spreading layers cannot be attained via conventional application of a plastic membrane by laminating or of a fibrous material membrane by gluing.

The sprayed spreading layer can be used for separating sample components of a body fluid such as, for example, blood cells. To effect separation, the spreading layer should have a nominal pore diameter of less than about 8 μm, or alternatively of no more than about 5 μm. Smaller pores, however, increase the time required for a sample to transit through the spreading layer. For this reason, pore diameters of less than about 20 μm are advantageous. As such, nominal pore diameters are generally no more than about 20 μm, or alternatively are from about 8 μm to about 15 μm. The nominal pore diameter of a membrane can be measured by bubble point measurements, which also are known as bubble pressure tests.

In one embodiment, the pore size of the spreading layer decreases towards the detection layer. Such an asymmetrical spreading layer can be produced by, for example, changing the spray parameters during spraying.

Spraying therefore allows for very small, discrete structures to be generated in an advantageous manner, which can be utilized, for example, to provide test elements on a lancet. In this manner, a detection layer can be applied by, for example, spraying it onto a lancet as a first step. Then, a spreading layer can be applied by spraying onto the detection layer in a further step. The use of micro-nozzles and/or masks allows for integration into a lancet of test elements that are so tiny that they could not be produced by laminating or produced only with very much effort. In this embodiment, the support of the test element can be the lancet body, which consists of, for example, metal.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 1 shows a schematic view of an illustrative embodiment of a test element for photometric testing of a body fluid sample.

FIG. 2 shows a schematic sectional view related to FIG. 1.

FIG. 3 shows another illustrative embodiment of a test element.

While the present inventions are susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments described herein and the claims below. Reference therefore should be made to the embodiments and claims for interpreting the scope of the invention. As such, it should be noted that the embodiments described herein may have advantages, effects, features and objects useful in solving other problems.

DESCRIPTION OF PREFERRED EMBODIMENTS

The methods and test elements now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the methods and test elements described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Methods and Test Elements

Figure 2:
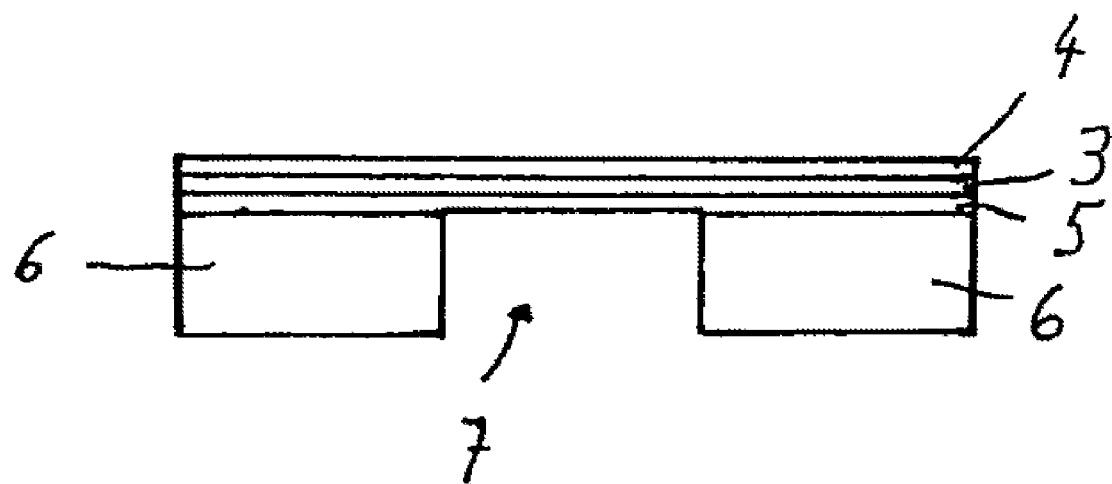

The test element 1 shown in FIGS. 1 and 2 is configured for photometric testing of a body fluid sample such as, for example, blood and/or interstitial fluid. Such a test element can be used to measure the concentration of glucose, lactate or other medically significant analytes.

For photometric determination of the concentration of an analyte, the test element 1 contains a test field 2. The test field has a detection layer 3 that includes detection reagents, which are not necessarily shown to scale in FIG. 2. When the detection reagents are exposed to the analyte, they effect a detection reaction that leads to a color change. The intensity of the change of color in this context depends on the analyte concentration such that photometric analysis of the color change allows the analyte concentration to be determined.

The detection layer 3 is covered by a polymeric spreading layer 4. The spreading layer 4 is a layer that spreads a body fluid sample applied to it. Fluid to be tested proceeds through the spreading layer 4 and then to the detection layer 3.

The detection layer 3 is arranged on a support 5. In an illustrative embodiment, the support 5 is a transparent plastic film. The support 5 can be arranged on a second support 6 such as, for example, a strip of plastic or paper. The second support 6 has a recess 7 that is covered by the support 5 of the detection layer 3. In this manner, a photometric measurement can proceed through the recess of the second support 6 and the transparent first support 5. Advantageously, the spreading layer 4 has no influence on the measurement in this case.

The spreading layer 4 shown in FIGS. 1 and 2 is produced by spraying a liquid, for example, by means of a pneumatic nozzle, onto the detection layer 3.

Polymers are sprayed onto the detection layer 3 to form a porous spreading layer 4. It is feasible just as well to spray monomers or a mixture of monomers and polymers onto the detection layer 3 and to polymerize them on the detection layer 3. Polymers also can be cross-linked and polymerized further after being applied by spraying, but this is not obligatory.

In some embodiments, monomers or polymers for forming the spreading layer 4 can be sprayed onto the detection layer 3 as an emulsion. In this instance, a phase inversion proceeds in droplets of the emulsion or upon impact on the detection layer 3. The monomers or polymers contained in the emulsion then can form the spreading layer 4, for example, as a membrane or a nonwoven fabric, and become cross-linked. In other embodiments, a solution, such as a polymer solution, is sprayed to form the spreading layer.

Regardless of whether an emulsion or a solution is applied by spraying, the molecules that then form the spreading layer 4 are sprayed together with a liquid that evaporates subsequently. The liquid can be a polar organic liquid such as, for example, an alcohol. It also is contemplated that aqueous liquids may be used, although the detection layer 4 might possibly be affected adversely by aqueous liquids. For this reason, polar organic liquids are preferred.

The spreading layer 4 can be produced from, for example, cellulose, modified cellulose, in particular hydroxypropylcellulose, cellulose nitrate or cellulose acetate, polyethylene glycol, polysulfone, polyethersulfone, polyolefin, polyurethane, polyamide, polyimide, polyacrylate, polycarbonate, polyester, polyether, polyvinylether, polyvinylester, polyvinylalcohol, polysiloxane or a mixture thereof containing one or more of the polymers. Substituted polymers of these classes are feasible just as well, such as, for example, polytetrafluoroethylene, and polymer mixtures such that copolymers are produced upon application by spraying.

The spreading layer 4 advantageously can be sprayed directly onto the detection layer 3. In this manner, the spreading layer 4 contacts the detection layer 3 (i.e., touches against it). In some embodiments, the spreading layer 4 can have a thickness of about 5 μm to about 10 μm, or even up to about 20 μm. As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The distance between the surface of the spreading layer 4 and the detection layer 3 being small is advantageous in that a body fluid sample applied to the spreading layer 4 can reach the detection layer 3 very quickly. The breakthrough time (i.e., the time for fluid applied to the spreading layer 4 to reach the detection layer 3) is less than one-tenth of a second. The thickness of the spreading layer 4 being low also is advantageous in that only very little fluid remains in the spreading layer 4 such that a very large fraction of the sample quantity is available for the detection reaction in the detection layer 3. Quantities as small as about 0.5 μm therefore are sufficient for determining the analyte concentration.

In some embodiments, a hydrophilic substance can be embedded in the spreading layer 4 such as, for example, a surfactant or other surface-active substance. The hydrophilic substance can be applied either by spraying together with the spreading layer or by being incorporated into the spreading layer 4 in a subsequent manufacturing step.

The spreading layer can have a nominal pore diameter of less than about 5 μm and typically of no more than about 2 μm. Alternatively, the nominal pore diameter can be of no more than about 1 μm or can be about 0.5 μm. In this manner, the spreading layer 4 can be used to remove, by filtration, sample components that interfere with the detection reaction or the analysis thereof such as, for example, blood cells. The porosity of the spreading layer 4 even can be asymmetrical in that the pore size decreases toward the detection layer 3.

Application of the spreading layer 4 by spraying can be used to produce layers with improved spreading behavior so that the surface area wetted by applying about 0.5 μl of a body fluid sample such as blood is twice as large as on a hydrophobic surface.

Figure 3:
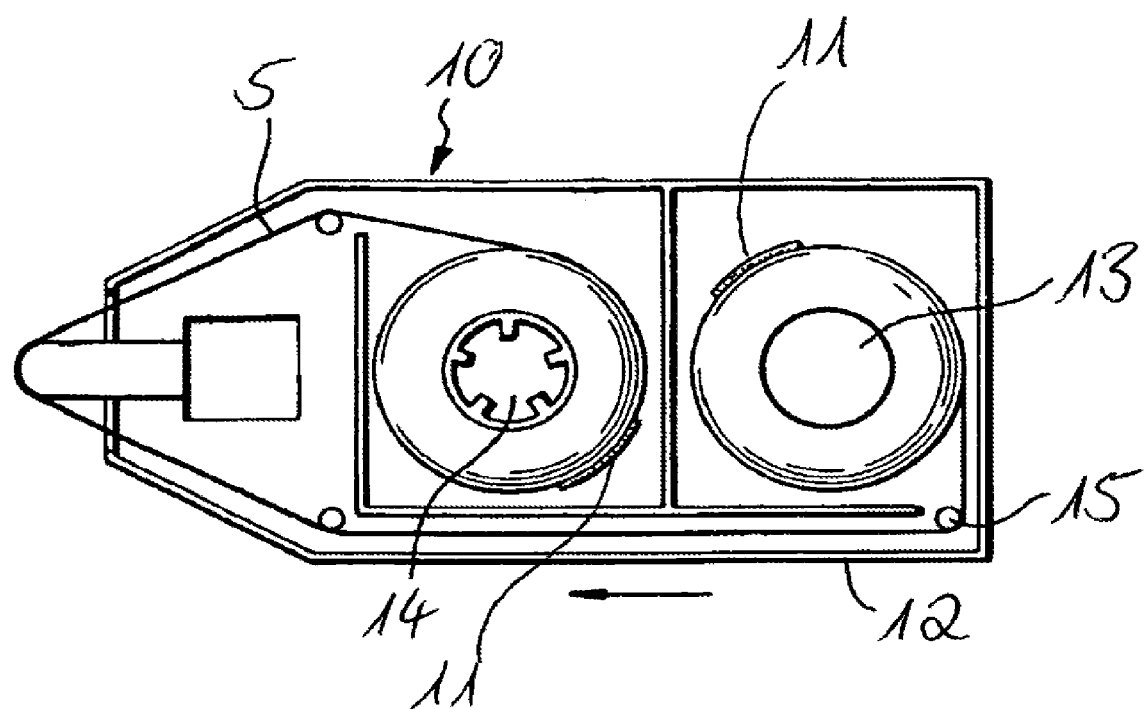

The test element shown in FIGS. 1 and 2 can be provided in the form of a test strip. For example, and as shown in FIG. 3, a test element for photometric testing of a body fluid sample can differ from the embodiment described above in that the support 5 is a tape that can be arranged such that it is reeled up into a tape cartridge 10. A tape cartridge 10 of this type allows a large number of body fluid samples to be tested. The improved adhesion and low thickness of a spreading layer applied by spraying are particularly advantageous for tape cartridges of this type since they make it easier to reel-up the support tape.

As further shown in FIG. 3, the support 5, which is provided as a tape, has multiple test fields 11 that each include a detection layer and a spreading layer covering the detection layer (i.e., can be made up like the embodiment according to FIGS. 1 and 2). The tape cartridge 10 has a housing 12, in which a bulk supply roll 13 is arranged on which the support 5 bearing unspent test fields 11 is reeled up in the form of a tape. Spent test fields are reeled up onto a drive reel 14 together with the support 5. Reeling-up the drive reel simultaneously reels-off the bulk supply reel such that the test fields 11 can be moved sequentially to a housing opening for use.

The tape cartridge 10 can include a chamber for the bulk supply reel 13. The drive reel 14 can be arranged outside the chamber of the bulk supply reel 13. In this manner, the bulk supply reel 13 with the sensitive detection reagents of the unspent test fields 11 is protected from detrimental ambient influences and, in particular, from moisture in spent test fields. The support 5, which is provided as a tape, can be guided on its path from the bulk supply reel 13 to the drive reel 14 by means of tape guiding elements 15 that define the tape transport pathway.

EXAMPLES

The invention will be more fully understood upon consideration of the following non-limiting examples, which are offered for purposes of illustration, not limitation.

Efficient spreading layers have been obtained, for example, as follows:

Bionate 80A UR (an aliphatic polyurethane, from DSM Biomedical Materials; Geleen, NL) was dissolved in tetrahydrofuran (an aliphatic ether, from Sigma-Aldrich; Steinheim, GER) at a concentration between 3-6% (m/m). To this solution, Tween 20 (a surfactant, polyoxyethylene(20)-sorbitan-monolaurate, alternative name poly(oxy-1,2-ethandiyl)-monododecanoic acid sorbitylester, from Sigma-Aldrich) or DONS (dioctylsulfosuccinate sodium salt, alternative name bis(2-ethylhexyl)-sulfosuccinate sodium salt, from Sigma-Aldrich) was added in an amount corresponding to about 3-5% (m/m) of the polymer content. The solution then was sprayed through a pneumatic rotary jet nozzle at a spraying pressure between about 2-4 bar. The consumption of polymer solution during the spraying process was about 2 ml/min.

The test element with the detection layer to be coated was arranged at a distance of 5 cm to 15 cm (e.g., about 10 cm) below the spray nozzle. The process was carried out at room temperature in a common laboratory ventilation hood (without controlling temperature and humidity). The polymer layer thus applied by spraying dried within a few seconds to form a film that adhered firmly to the detection layer.

The spraying process was carried out with either a static test element or a moving test element. For coating the moving test element, the test element was fixed in place on a cylinder, and the cylinder was rotated below the spray nozzle (e.g., at about 100-120 rpm). The spreading layers applied in both static and mobile manner showed an efficient spreading effect.

The layer thickness of the sprayed spreading layer was varied by selecting the spraying time. A spraying time of about 2 seconds produced spreading layers with a layer thickness in the range of about 2-5 μm. At a spraying time of about 10 seconds, the layer thickness of the spreading layer was in the range of about 8-10 μm. Longer spraying times allowed the layer thickness to be adapted according to need to values of, for example, 20 μm, 40 μm or even 100 μm.

The efficiency of the spreading layer was checked by dripping different volumes of blood ranging from 0.05 μl to 2.0 μl onto the uncoated detection layer versus the spreading layer-coated detection layer. For example, a 0.5 μl droplet of blood had a diameter of about 1.5 mm on an uncoated detection layer and did not spread on the hydrophobic surface. There remained a dome-shaped blood residue with a contact angle of about 40°. In contrast, the 0.5 μl droplet of blood had a diameter of about 2.8 mm to about 3.1 mm on the detection layer coated with the spreading layer sprayed onto it and spread completely (i.e., no residual blood remained visible (contact angle 0°)). Accordingly, the sprayed spreading layer increased the surface of the detection layer that was wetted by blood by about four-fold. The very efficient improvement of the spreading behavior was detected regardless of the layer thickness of the spreading layer (i.e., was evident with thin spreading layers in, e.g., the range of about 2-5 μm) as well as with thicker spreading layers (in the range of about 20-40 μm).

Moreover, it was found that the spreading behavior improved through the sprayed-on spreading layer regardless of the blood volume for blood volumes in the relevant range of 0.05-2 μl. The thickness of the layer was determined through optical digital microscopy (incident light) using one cross-section each of the coated test elements. This was tested using a Keyence VHX-1000 microscope as the measuring device. The efficiency of the spreading layer was determined in a corresponding manner, namely by optical digital microscopy (incident light) of the wetted region of a test element after the application of a blood sample. The contact angles were determined using a Kruss DAS 100 contact angle measuring device (Kruss GmbH; Hamburg, Del.).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

LISTING OF REFERENCE NUMBERS

1. Test element
2. Test field
3. Detection layer
4. Spreading layer
5. Support
6. Second support
7. Recess
10. Tape cartridge
11. Test field
12. Housing
13. Bulk supply reel
14. Drive reel
15. Tape guiding element

The invention claimed is:

1. A test element for detecting an analyte in a body fluid sample, the test element comprising:
   a support;
   a detection layer applied to the support; and
   a polymeric spreading layer covering the detection layer, wherein the polymeric spreading layer covering the detection layer is sprayed onto the detection layer to form a non-fibrous nonwoven fabric.

2. The test element of claim 1, wherein the spreading layer has a thickness selected from the group consisting of about 5 μm, about 10 μm, about 12 μm and about 20 μm.

3. The test element of claim 1, wherein the spreading layer contacts the detection layer.

4. The test element of claim 1, wherein the entire spreading layer is asymmetrical in that nominal pore sizes or diameters decrease in a direction toward the detection layer, and wherein the nominal pore sizes or diameters are about 8 μm to about 15 μm.

5. The test element of claim 1, wherein the spreading layer has a breakthrough time that is less than about one-tenth of a second.

6. The test element of claim 1, wherein the support is a tape wound into a reel in a tape cartridge.

7. The test element of claim 1, wherein the polymeric spreading layer comprises a polymer selected from the group consisting of polyethylene glycol, polyvinylalcohol, polyolefin, polyurethane, polyamide, polyimide, polyacrylate, polycarbonate, polyester, polyether, polyvinylether, polyvinylester, polyvinylalcohol and polysiloxane.

8. The test element of claim 1, wherein the spreading layer produces a mechanical stress upon the detection layer consistent with having been sprayed onto the detection layer.

* * * * *